(12) United States Patent
Christensen et al.

(10) Patent No.: US 7,825,215 B1
(45) Date of Patent: Nov. 2, 2010

(54) SUBSTITUTED NUCLEIC ACID MIMICS

(75) Inventors: Leif Christensen, Charlottenlund (DK); Henrik Frydenlund Hansen, Radovre (DK); Peter E. Nielsen, Hjortevaenget 509, 2980 Kokkedal (DK)

(73) Assignee: Peter E. Nielsen, Federiksberg (DK)

( * ) Notice: Subject to any disclaimer, the term of this patent is extended or adjusted under 35 U.S.C. 154(b) by 0 days.

(21) Appl. No.: 08/612,661

(22) Filed: Mar. 8, 1996

Related U.S. Application Data

(63) Continuation-in-part of application No. 08/595,387, filed on Feb. 1, 1996, now Pat. No. 5,773,571, which is a continuation-in-part of application No. 08/054,363, filed on Apr. 26, 1993, now Pat. No. 5,539,082.

(51) Int. Cl.
*C07K 2/00* (2006.01)
*A61K 38/00* (2006.01)
*C07K 1/00* (2006.01)
*C12Q 1/68* (2006.01)
*G01N 33/566* (2006.01)
*C07H 21/02* (2006.01)

(52) U.S. Cl. .................. 530/300; 530/350; 435/6; 436/501; 536/23.1

(58) Field of Classification Search .............. 435/6, 435/810; 436/501; 514/2, 44; 530/300, 530/350; 536/23.1, 24.1, 24.3–24.33; 935/77, 935/78
See application file for complete search history.

(56) References Cited

U.S. PATENT DOCUMENTS

| | | | |
|---|---|---|---|
| 4,828,979 A | | 5/1989 | Klevan et al. .................. 435/6 |
| 5,635,352 A | * | 6/1997 | Urdea et al. .................... 435/6 |
| 5,705,333 A | * | 1/1998 | Shah et al. ...................... 435/6 |
| 6,180,767 B1 | | 1/2001 | Wickstrom et al. ......... 536/22.1 |

FOREIGN PATENT DOCUMENTS

| | | |
|---|---|---|
| EP | 0 646 596 A1 | 4/1995 |
| EP | 0 672 700 A1 | 9/1995 |
| EP | 0 672 701 A1 | 9/1995 |
| WO | 86/05518 * | 9/1986 |
| WO | 92/20702 * | 11/1992 |
| WO | 92/20703 * | 11/1992 |
| WO | WO 92/20702 | 11/1992 |
| WO | WO 92/20703 | 11/1992 |
| WO | WO 93/25706 | 12/1993 |
| WO | WO 95/01369 A1 | 1/1995 |
| WO | WO 95/01370 | 1/1995 |

OTHER PUBLICATIONS

Christensen et al., Journal of Peptide Science, vol. 3 pp. 175-183, 1995.*
Webb et al., J. Am. Chem. Soc., vol. 108, pp. 2764-2765, 1986.*
Summerton et al., J. Mol. Biol., vol. 122, pp. 145-162, 1978.*
Inoue et al., Nucleic Acids Research, vol. 13, No. 19, pp. 7119-7128, 1985.*
Christensen et al. Solid-Phase Synthesis of Peptide Nucleic Acids *Journal of Peptide Science* 1995 3:175-183.
Spalholz et al. Bovine Papillomavirus Transcriptional Regulation: Localization of the E2-Responsive Elements of the Long Control Region *Journal of Virology* 1987, vol. 61.
Krotz, A.H., et al., "Synthesis of 'Retro-Inverso' peptide nucleic acids: 1. Characterization of the monomers," *Tetrahedron Letts.*, 1995, 36(38), 6937-6940.
Krotz, A.H., et al., "Synthesis of 'Retro-Inverso' peptide nucleic acids: 2. Oligomerization and stability," *Tetrahedron Letts.*, 1995, 36(38), 6941-6944.
Petersen, K.H., et al., "A PNA-DNA linker synthesis of *N*-((4,4'-dimethoxytrityloxy)ethyl)-*N*-(thymin-1 -ylacetyl)glycine," *Boorganic & Medicinal Chem. Letts.*, 1995, 5(11), 1119-1124.

* cited by examiner

*Primary Examiner*—Ardin Marschel
*Assistant Examiner*—Gregg Polansky
(74) *Attorney, Agent, or Firm*—ISIS Patent Department

(57) ABSTRACT

Compositions and methods are provided for the nucleic acid mimic determination of nucleic acids. The compositions and methods may be used in the diagnosis and treatment of diseases amenable through modulation of nucleic acids which encode proteins that are implicated in disease states. In accordance with preferred embodiments, mimics are comprised of non-naturally occurring backbones to which are appended modified heterocyclic bases. Such bases preferably have sterically bulky substituents 1, 2, or 3 atoms removed from the sites of attachment to the backbone.

11 Claims, 2 Drawing Sheets

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 10 bases
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:1:

AAAAGGAGAG                                                                 10

-continued (2) INFORMATION FOR SEQ ID NO:2:

(i) SEQUENCE CHARACTERISTICS:
        (A) LENGTH: 10 bases
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:2:

GAGAGGAAAA         10

(2) INFORMATION FOR SEQ ID NO:3:

(i) SEQUENCE CHARACTERISTICS:
        (A) LENGTH: 10 bases
        (B) TYPE: nucleic acid
        (C) STRANDEDNESS: single
        (D) TOPOLOGY: linear (ii) MOLECULE TYPE: PNA (iii) HYPOTHETICAL: NO (iv) ANTI-SENSE: YES (xi) SEQUENCE DESCRIPTION: SEQ ID NO:3:

TTTTCCTCTC         10

(2) INFORMATION FOR SEQ ID NO:4:

(i) SEQUENCE CHARACTERISTICS:
        (A) LENGTH: 10 bases
        (B) TYPE: nucleic acid
        (C) STRANDEDNESS: single
        (D) TOPOLOGY: linear (ii) MOLECULE TYPE: PNA (iii) HYPOTHETICAL: NO (iv) ANTI-SENSE: YES (xi) SEQUENCE DESCRIPTION: SEQ ID NO:4:

TTTTCNTCTC         10

(2) INFORMATION FOR SEQ ID NO:5:

(i) SEQUENCE CHARACTERISTICS:
        (A) LENGTH: 10 bases
        (B) TYPE: nucleic acid
        (C) STRANDEDNESS: single
        (D) TOPOLOGY: linear (ii) MOLECULE TYPE: PNA (iii) HYPOTHETICAL: NO (iv) ANTI-SENSE: YES (xi) SEQUENCE DESCRIPTION: SEQ ID NO:5:

TTTTCNTNTC         10

(2) INFORMATION FOR SEQ ID NO:6:

```
        (i) SEQUENCE CHARACTERISTICS:
            (A) LENGTH: 10 bases
            (B) TYPE: nucleic acid
            (C) STRANDEDNESS: single
            (D) TOPOLOGY: linear (ii) MOLECULE TYPE: PNA (iii) HYPOTHETICAL: NO (iv) ANTI-SENSE: YES (xi) SEQUENCE DESCRIPTION: SEQ ID NO:6:

TTTTNNTCTC                                                                  10

(2) INFORMATION FOR SEQ ID NO:7:

(i) SEQUENCE CHARACTERISTICS:
            (A) LENGTH: 10 bases
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:7:

GTAGGTCACT                                                                  10

(2) INFORMATION FOR SEQ ID NO:8:

(i) SEQUENCE CHARACTERISTICS:
            (A) LENGTH: 10 bases
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:8:

GTAGATCACT                                                                  10

(2) INFORMATION FOR SEQ ID NO:9:

(i) SEQUENCE CHARACTERISTICS:
            (A) LENGTH: 10 bases
            (B) TYPE: nucleic acid
            (C) STRANDEDNESS: single
            (D) TOPOLOGY: linear (ii) MOLECULE TYPE: PNA (iii) HYPOTHETICAL: NO (iv) ANTI-SENSE: YES (xi) SEQUENCE DESCRIPTION: SEQ ID NO:9:

AGTCACCTAC                                                                  10

(2) INFORMATION FOR SEQ ID NO:10:

(i) SEQUENCE CHARACTERISTICS:
            (A) LENGTH: 10 bases
            (B) TYPE: nucleic acid
```

```
        (C) STRANDEDNESS: single
        (D) TOPOLOGY: linear (ii) MOLECULE TYPE: PNA (iii) HYPOTHETICAL: NO (iv) ANTI-SENSE: YES (xi) SEQUENCE DESCRIPTION: SEQ ID NO:10:

AGTCANCTAC                                                    10
```

SUBSTITUTED NUCLEIC ACID MIMICS

This patent application is a continuation-in-part of application Ser. No. 08/595,387, filed Feb. 1, 1996 (now U.S. Pat. No. 5,773,571), which is a continuation-in-part of Ser. No. 08/054,363, filed Apr. 26, 1993 (now U.S. Pat. No. 5,539,082).

FIELD OF THE INVENTION

This invention is directed to the synthesis and use of nucleic acid mimics containing one or more heterocyclic base moieties substituted by chemical groups in order to diminish or prevent the formation of triplexes. This effect can be used to design antisense or probe reagents that avoid forming triplexes.

BACKGROUND OF THE INVENTION

In the art, there are known several nucleic acid mimics having nucleobases bound to backbones other than the naturally occurring ribonucleic acid or deoxyribonucleic acid backbones having the ability to bind to nucleic acids having a nucleobase sequence complementary to the base sequence of the nucleic acid mimic. Among these, only the peptide nucleic acids (PNA's) as described, for example, in WO 92/20702 have demonstrated a likelihood for potential use as therapeutic and diagnostic reagents. This may be due to their ability to bind nucleic acids (NAs) of complementary nucleobase sequence with a higher affinity than shown by the corresponding wild-type nucleic acid.

One of the unique properties of PNAs is their ability to form $PNA_2$-NA triplexes that are more stable than the corresponding PNA-NA duplexes. This ability can be used advantageously for various purposes including PCR clamping (WO 93/25706). However, there are some drawbacks for applications that require sequence selection, because such selection would be biased for triplex forming sequences. Therefore, there is a need for PNAs that do not form such triplexes.

OBJECTS OF THE INVENTION

It is an object of this invention to provide substituted nucleic acid mimics that do not preferentially form triplexes with nucleic acids.

It is a further object of this invention to provide methods for sequence selective determination of nucleic acids.

It is yet a further object of this invention to provide therapeutic, diagnostic and research reagents that can modulate the expression of nucleic acids which encode proteins suspected of causing or indicating the existence of a disease state.

BRIEF DESCRIPTION OF THE INVENTION

In accordance with this invention there are provided nucleic acid mimics containing one or more heterocyclic bases substituted by a sterically bulky substituent at a position which is 1, 2 or 3 atoms removed from the atom of the base which is attached to the backbone.

Further there are provided methods for disfavouring the formation of triplex structures comprising a nucleic acid strand and two strands of a nucleic acid mimic, having a base sequence complementary to the nucleic acid strand. Such methods include incubating a mixture of the nucleic acid and the nucleic acid mimic under conditions suitable for forming a nucleic acid/nucleic acid mimic duplex. The formation of triplexes is avoided by providing sterically bulky substituents on the nucleic acid mimic which are located at positions that would be in close proximity to each other if bound to nucleic acid in a triplex.

In accordance with this invention there are provided methods for the determination of a nucleic acid by providing a nucleic acid mimic substituted at positions which are 1, 2 or 3 atoms removed from the atom of the base which is attached to the backbone. Said nucleic acid mimic is incubated with the nucleic acid under conditions suitable for the formation of a duplex between the nucleic acid mimic and the nucleic acid. The occurrence of the duplex is related to the identity or existence of the nucleic acid.

The present invention provides nucleic acid mimics for modulating the expression of nucleic acids that encode proteins which are suspected of producing a disease state in mammals. The nucleic acid mimics of this invention can be used in therapeutics, diagnostics and as research reagents.

One favourable aspect of this invention is that nucleic acid mimics substituted as described herein substantially retain the ability to form duplexes with good efficiency and discrimination comparable to the corresponding unsubstituted nucleic acid mimic.

DETAILED DESCRIPTION OF THE INVENTION

Figure 1:
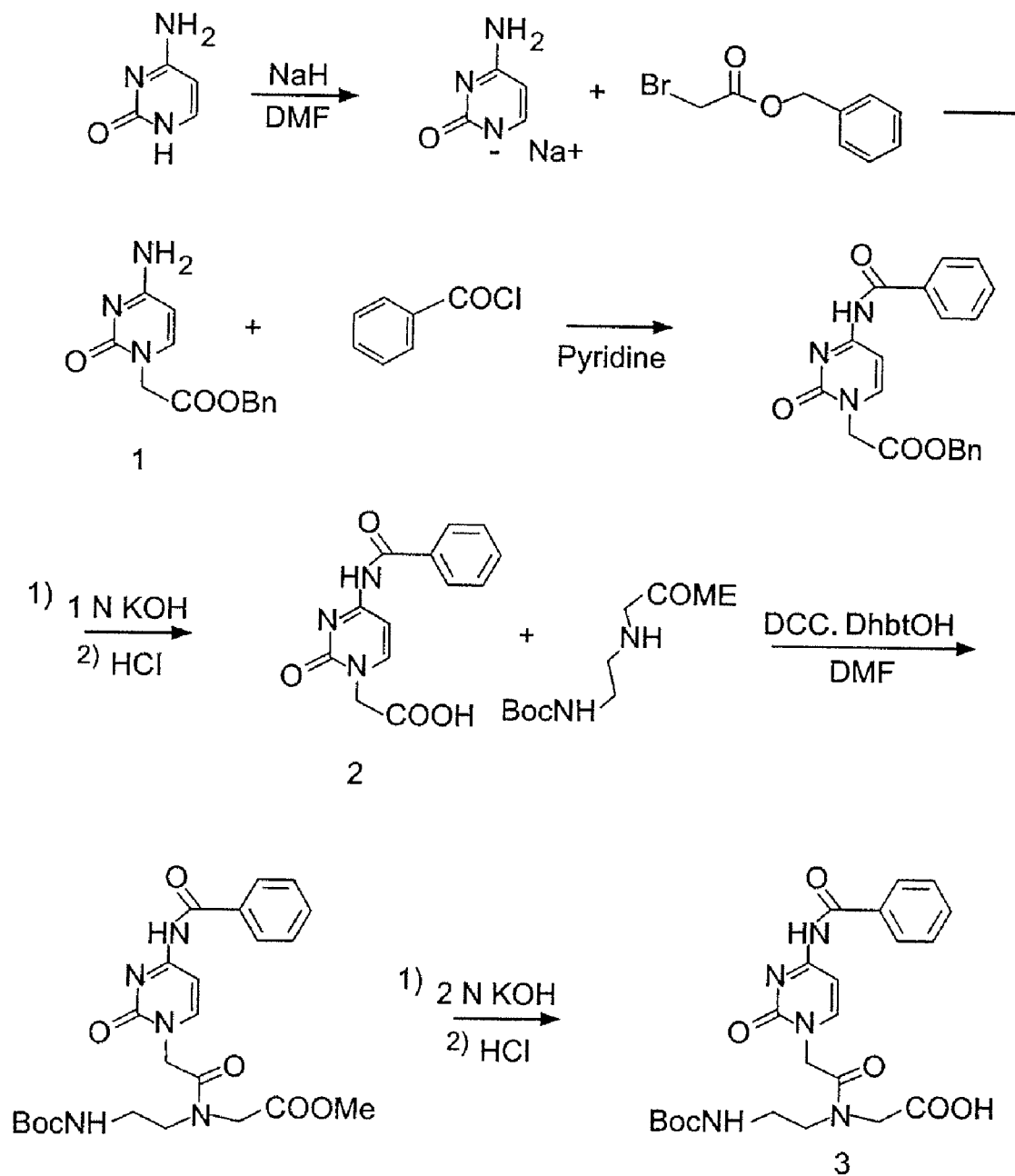
FIG. 1 is a schematic illustrating an exemplary synthesis of a PNA monomer containing cytosine substituted at the $N^4$ position.

In accordance with this invention, novel compounds are provided that are useful for disfavouring the formation of triplexes with nucleic acids. A nucleic acid mimic in accordance with the invention is a molecule having a sequence of modified heterocyclic bases, preferably naturally occurring bases, e.g. those which occur in "wild-type" nucleic acids, bound to a non-naturally occurring backbone. The nucleic acid mimics bind to a nucleic acid having a complementary base sequence through base pairing.

Preferred nucleic acid mimics are molecules wherein the base moieties are bound to the backbone via an amine nitrogen atom of the backbone. Preferred backbone structures for the mimics are described in WO 92/20702, U.S. patent application Ser. No. 08/054,363, filed Apr. 26, 1993, U.S. patent application Ser. No. 08/319,411, filed Oct. 6, 1994 and U.S. patent application Ser. No. 08/366,231, filed Dec. 28, 1994. The above-referenced disclosures are herein incorporated by reference.

Heterocyclic bases of the nucleic acid mimics of the present invention are heterocyclic moieties that are able to base pair with nucleobases of a nucleic acid by hydrogen bonding. In the case of triplex formation, two kinds of interactions are involved: Watson-Crick binding and Hoogsteen binding. The formation of triplexes between PNA and NA is described in WO 95/01370.

The term "heterocyclic moiety" or "heterocyclic base" includes the naturally occurring purine and pyrimidine nucleobases. For the purpose of this invention, the term "pyrimidine" refers to any 1,3-diazine irrespective of its substituents. The naturally occurring pyrimidine nucleobases are cytosine, thymine and uracil. Naturally occurring purine nucleobases include adenine and guanine. The term "heterocyclic moiety" or "heterocyclic base" also includes non-naturally occurring nucleobases. An example of a non-naturally occurring base is a base in which any of the ring atoms of the nucleobases is replaced by another atom. For example, CH may be replaced by N and vice versa. Such modifications can occur at more than one position. Another example of a non-naturally occurring base is a base in which the 2- and 4-substituents of a naturally occurring base are reversed. Structures of naturally and non-naturally occurring pyrimidine bases are shown below (the third structure from the left is that of a non-naturally occurring pyrimidine base known as pseudo-isocytosine):

In the invention, the heterocyclic moiety is attached to the backbone at a specific ring position of the heterocycle. In the case of substituted naturally occurring nucleobases, this position is preferably occupied by a nitrogen atom. According to this invention, the sterically bulky substituent can be attached to the heterocyclic moiety at a position which is 1, 2 or 3 atoms removed from the position of attachment of the heterocyclic moiety to the backbone. In case of the pyrimidine bases, positions conventionally numbered as ring position 4, 5 and 6 are preferred. The 4-position is most preferred for attaching a bulky substituent. Some effect on triplex formation may also occur when the substituent is attached to the 5- and 6-positions, but in this case, the substituents should be sterically bulkier than substituents located at position 4. In the case of non-naturally occurring bases, positions corresponding to pyrimidine positions 4, 5 and 6 in their spatial orientation are also preferred. In case of substitution on the 5-position of a non-naturally occurring base, the triplex formation is pH dependent as it is for a naturally occurring base such as cytosine. Duplex formation is likely not effected by pH in any case.

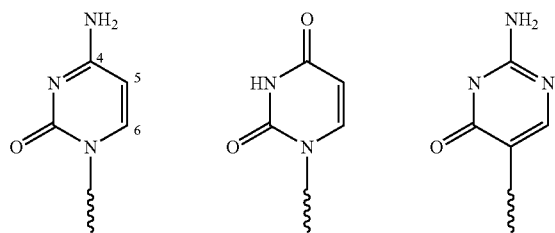

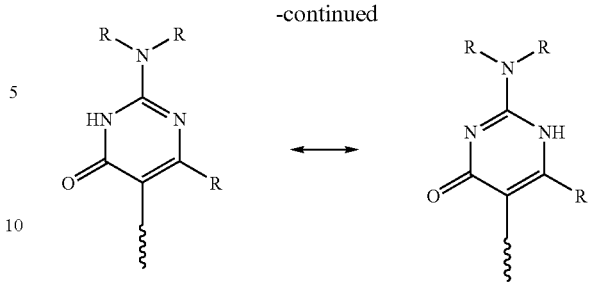

Shown above are formulae of heterocyclic bases having substituents designated R. Each R can independently be H, —NO, —NO$_2$, —SO$_3$, —CN, —OH, —SH, —PO$_3^{2-}$, —COOH, —R', —F, —Cl, —Br, —I, —O—R', —S—R', —N(R')$_2$, —C(R')$^3$, —C(=X)(R'), C(=X)(—Y—R'), S(=Z)$_{1-2}$(—Y—R'), in which Z is O, X is O, S or NH, and Y is O, S or NH, wherein at least one R is a sterically bulky group. Preferred bulky groups contain 3 non-hydrogen atoms or more, most preferred bulky groups contain 6 non-hydrogen atoms or more and are preferably cyclic and/or aromatic. It will be apparent from the description of this invention that these preferred definitions apply to the case wherein at least one R substituent is different from hydrogen. In case 2 or more R groups are bulky, the spatial requirements for achieving inhibition may be reduced, for example, from 6 atoms to 3 atoms.

It is preferred that R groups are acyl groups, especially aromatic acyl groups. It is especially preferred that the acyl groups be bound to a nitrogen atom at position 4 of a pyrimidine base. An especially preferred acyl group is the benzoyl group.

R' is preferably selected from H; alkyl, alkenyl or alkynyl (each having from 1-50 C atoms); aryl, naphthyl, biphenyl or tolyl (each having from 6-50 C atoms). These groups may be straight or branched chain, symmetric or asymmetric, chiral or achiral, and may contain one or more heteroatoms selected from N, NH, S and O, and may also comprise fused aromatic systems. R' may be heterocyclic, including pyridyl, imidazolyl, pyrimidinyl, pyridazinyl, quinolyl, acridinyl, imidazolyl, pyrrolyl, furanyl, thienyl, isoxazolyl, oxazolyl, thiazolyl or biotinyl and may be bound or fused to any available position.

R' may be substituted, preferentially with one or more lower organic groups (up to 10 carbon-atoms) or derivatives thereof which enhance the triplex inhibiting effect or are otherwise useful herein. These may be groups such as alkyl, alkenyl, alkynyl, aryl, naphthyl, biphenyl, tolyl, benzyl, and groups such as —NO, —NO$_2$, —SO$_3$, —CN, —OH, —SH, —PO$_3^{2-}$, —COOH, —F, —Cl, —Br, and —I.

Compounds of the present invention can be conveniently prepared according to the methods described in WO 92/20702. An especially preferred method of synthesis uses, in a first step, the synthesis of the base substituted by the sterically bulky substituent, preferably having also attached a reactive group and/or a linker moiety for attachment of the modified base to a monomeric backbone unit, for example, protected N-aminoethylglycine. In a second step, bases are attached via the linker moiety to a nitrogen atom at the preformed and protected monomeric backbone unit. In a third step, the base-containing monomer is prepared for oligomerization with other bases containing monomeric backbone units or an already formed oligomer, e.g. cleaving of protecting groups at one end of the backbone unit and/or activating

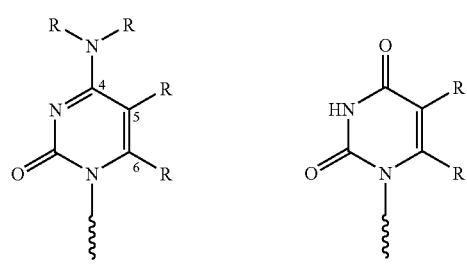

this end for oligomerization. In a fourth step, the base-containing monomers are oligomerized depending upon the sequence requirements for complementarity for duplex formation with a complementary nucleic acid.

Preferred monomeric backbone units that may be protected with a protecting group appropriate for the active groups during synthesis of the monomeric backbone unit are compounds of the general formula:

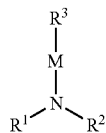

wherein:
  $R^1$ is $C_1$-$C_4$ alkyl substituted by —COOP$^1$, —NHP$^1$, —OP$^1$ or SP$^1$, wherein P$^1$ is hydrogen or a protecting group;
  $R^2$ is $C_1$-$C_4$ alkyl substituted by —COOP$^2$, —NHP$^2$, —OP$^2$ or SP$^2$, wherein P$^2$ is hydrogen or a protecting group;
  M is a naturally or non-naturally occurring heterocyclic moiety bound by a linker to nitrogen, said linker being 1-3 atoms in length; and
  $R^3$ is a sterically bulky substituent containing at least 3 or more non-hydrogen atoms.

Monomers which are not substituted by $R^3$ are disclosed in WO 92/20702. In a preferred case, $R^1$ contains the group —COOP$^1$ and $R^2$ contains the group —NHP$^2$, wherein the protecting groups (P$^1$ and P$^2$) are cleavable under different reaction conditions from each other.

For example, in certain preferred embodiments, peptide nucleic acid backbones may be employed. Such backbones have the general formula (I):

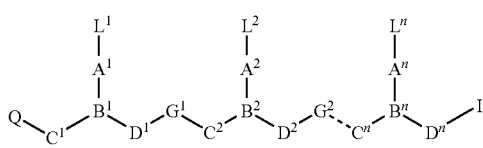

wherein:
  n is at least 2,
  each of $L^1$-$L^n$ is independently selected from the group consisting of hydrogen, hydroxy, ($C_1$-$C_4$)alkanoyl, naturally occurring nucleobases, non-naturally occurring nucleobases, aromatic moieties, DNA intercalators, nucleobase-binding groups, heterocyclic moieties, and reporter ligands, at least one of $L^1$-$L^n$ being a naturally- or non-naturally-occurring nucleobase substituted with a sterically bulky group as described herein;
  each of $C^1$-$C^n$ is $(CR^6R^7)_y$, where $R^6$ is hydrogen and $R^7$ is selected from the group consisting of the side chains of naturally occurring alpha amino acids, or $R^6$ and $R^7$ are independently selected from the group consisting of hydrogen, ($C_2$-$C_6$)alkyl, aryl, aralkyl, heteroaryl, hydroxy, ($C_1$-$C_6$)alkoxy, ($C_1$-$C_6$)alkylthio, NR$^3$R$^4$ and SR$^5$, where $R^3$ and $R^4$ are as defined above, and $R^5$ is hydrogen, ($C_1$-$C_6$)alkyl, hydroxy-, alkoxy-, or alkylthio-substituted ($C_1$-$C_6$)alkyl, or $R^6$ and $R^7$ taken together complete an alicyclic or heterocyclic system;

each of $D^1$-$D^n$ is $(CR^6R^7)_z$ where $R^6$ and $R^7$ are as defined above;
each of y and z is zero or an integer from 1 to 10, the sum y+z being greater than 2 but not more than 10;
each of $G^1$-$G^{n-1}$ is —NR$^3$CO—, —NR$^3$CS—, —NR$^3$SO— or —NR$^3$SO$_2$—, in either orientation, where $R^3$ is as defined above;
each pair of $A^1$-$A^n$ and $B^1$-$B^n$ are selected such that:
  (a) A is a group of formula (IIa), (IIb) or (IIc) and B is N or R$^3$N$^+$; or
  (b) A is a group of formula (IId) and B is CH;

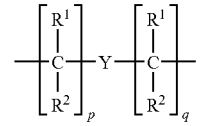

(IIa)

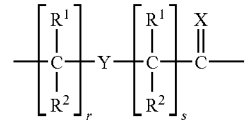

(IIb)

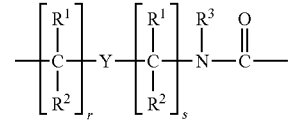

(IIc)

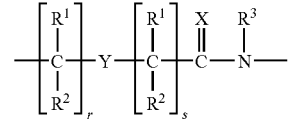

(IId)

where:
  X is O, S, Se, NR$^3$, CH$_2$ or C(CH$_3$)$_2$;
  Y is a single bond, O, S or NR$^4$;
  each of p and q is zero or an integer from 1 to 5, the sum p+q being not more than 10;
  each of r and s is zero or an integer from 1 to 5, the sum r+s being not more than 10;
  each $R^1$ and $R^2$ is independently selected from the group consisting of hydrogen, ($C_1$-$C_4$)alkyl which may be hydroxy- or alkoxy- or alkylthio-substituted, hydroxy, alkoxy, alkylthio, amino and halogen;
  each of $R^3$ and $R^4$ independently are hydrogen, a conjugate, ($C_1$-$C_4$)alkyl, hydroxy- or alkoxy- or alkylthio-substituted ($C_1$-$C_4$)alkyl, hydroxy, alkoxy, alkylthio or amino; $G^1$-$G^{n-1}$ is —NR$^3$CO—, —NR$^3$CS—, —NR$^3$SO— or —NR$^3$SO$_2$—, in either orientation, where $R^3$ is as defined above;
  Q is —CO$_2$H, —CONR'R", —SO$_3$H or —SO$_2$NR'R" or an activated derivative of —CO$_2$H or —SO$_3$H; and
  I is —NHR'''R'''' or —NR'''C(O)R'''', where R', R", R''' and R'''' are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers.

In certain embodiments, at least one A is a group of formula (IIc) and B is N or R$^3$N$^+$. In other embodiments, A is a group of formula (IIa) or (IIb), B is N or R$^3$N$^+$, and at least one of y or z is not 1 or 2.

Some preferred peptide nucleic acids have general formula (IIIa) or (IIIb):

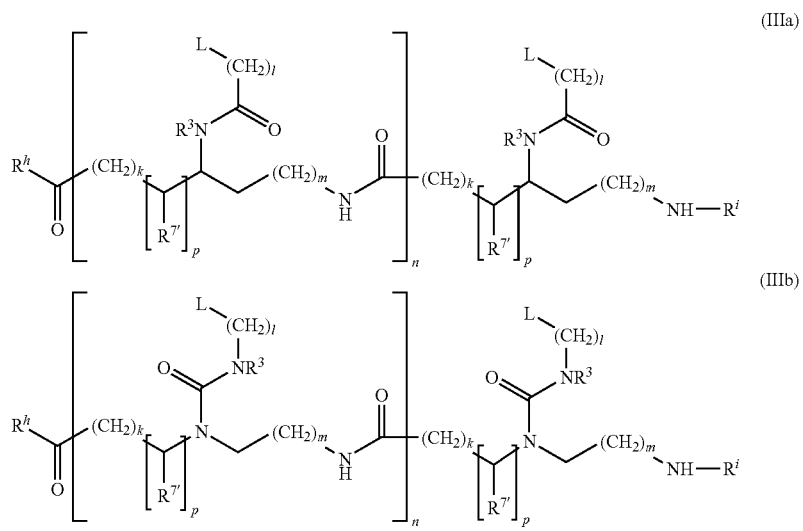

wherein:
each L is independently selected from the group consisting of hydrogen, phenyl, heterocyclic base moieties, including those substituted with a sterically bulky group or groups, naturally occurring nucleobases, and non-naturally occurring nucleobases;
each $R^{7'}$ is independently selected from the group consisting of hydrogen and the side chains of naturally occurring alpha amino acids;
n is an integer from 1 to 60;
each of k, l, and m is independently zero or an integer from 1 to 5;
p is zero or 1;
$R^h$ is OH, $NH_2$ or —$NHLysNH_2$; and
$R^i$ is H or $COCH_3$.

Particularly preferred are compounds having formula (IIIa) or (IIIb) wherein each L is independently selected from the group consisting of the nucleobases thymine (T), adenine (A), cytosine (C), guanine (G) and uracil (U), especially where one or more are modified with a sterically bulky substituent in accordance with this invention, k and m are zero or 1, and n is an integer from 1 to 30, in particular from 4 to 20.

The peptide nucleic acids of the invention can be synthesized by adaptation of standard peptide synthesis procedures, either in solution or on a solid phase. The synthons used are specially monomer amino acids or their activated derivatives, protected by standard protecting groups. The oligonucleotide analogs also can be synthesized by using the corresponding diacids and diamines.

Thus, monomer synthons useful for incorporation into PNA of the preceding formulae include those selected from the group consisting of amino acids, diacids and diamines, having general formulae:

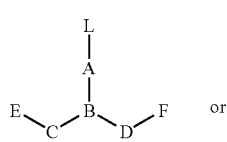
(IV)

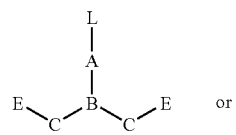
(V)

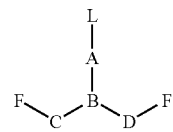
(VI)

wherein L, A, B, C and D are as defined above, except that any amino groups therein may be protected by amino protecting groups; E is COOH, CSOH, SOOH, $SO_2OH$ or an activated derivative thereof; and F is $NHR^3$ or $NPgR^3$, where $R^3$ is as defined above and Pg is an amino protecting group.

Preferred monomer synthons according to the invention include those having formula (VIIIa)-(VIIIc):

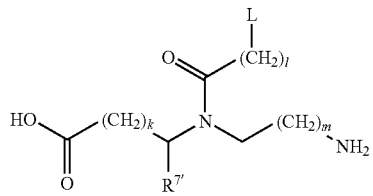
(VIIIa)

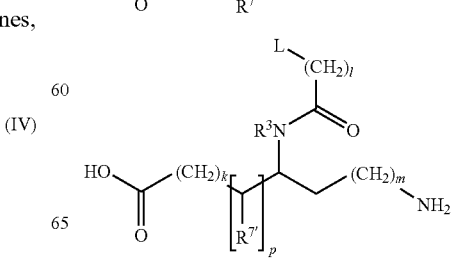
(VIIIb)

-continued

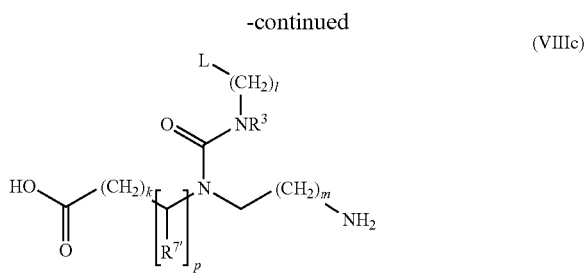

(VIIIc)

or amino-protected and/or acid terminal activated derivatives thereof, wherein L is selected from the group consisting of hydrogen, phenyl, heterocyclic moieties, naturally occurring nucleobases, and non-naturally occurring nucleobases; and $R^{7'}$ is selected from the group consisting of hydrogen and the side chains of naturally occurring alpha amino acids.

Also useful in the present invention are chiral PNA backbones. Such backbones are preferably derived from two or more monomers, at least one of which contain a aliphatic cyclic structure. Representative of such monomers are those of formula:

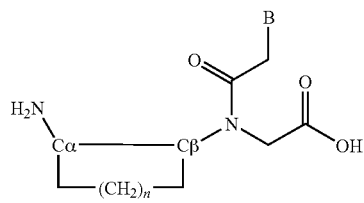

wherein:
B is a naturally or non-naturally occurring nucleobase which may be substituted with a sterically bulky group in accordance with this invention;
at least one of Cα or Cβ is in the S configuration; and
n is 0, 1, 2, or 3.

In preferred embodiments Cα and Cβ are in the S configuration. In further preferred embodiments of the invention B is adenine, cytosine, guanine, thymine, or uracil. In more preferred embodiments n is 2.

In further preferred embodiments the peptide nucleic acid oligomers contain at least one peptide nucleic acid monomer having a (2-aminoethyl)glycine backbone with a chiral center in the ethyl portion of the backbone. The monomer is incorporated into peptide nucleic acid oligomers at a position corresponding to a region of variability in the target molecule.

One nucleic acid mimic can contain one or more nucleobases modified as described above. It was found that increasing the number of nucleobases containing sterically bulky substituents within one nucleic acid mimic inhibited triplex formation while retaining the ability to form duplexes.

In order to achieve the inhibition of triplex formation, the nucleic acid mimic and the position of attachment of the sterically bulky group are chosen such that the heterocyclic bases to which the sterically bulky substituent is attached would be located in close proximity to each other when bound to the nucleic acid, were a triplex to form. Preferably the substituted bases on the nucleic acid mimics should, in the hypothetical triplex, be located on the same side, i.e. base pairing to the same nucleobase of the nucleic acid strand. This case wherein the substituted bases of the mimic would base pair to the same base on the nucleic acid strand will be termed as "opposed". That the substituted bases would have to base pair with a predefined base on the nucleic acid strand can be achieved by choosing the base sequence and orientation of the mimics such that only the triplex formation could occur in a way which is inhibited by the use of the sterically bulky substituents.

The compounds of the present invention can be used in methods for the determination of a nucleic acid comprising a nucleic acid mimic substituted at positions which are 1, 2 or 3 atoms removed from the atom of the base which is attached to the backbone, incubating said nucleic acid mimics and said nucleic acid under conditions suitable for the formation of a duplex between said nucleic acid mimic and said nucleic acid and determining the occurrence of said duplex as a measure of the occurrence of said nucleic acid. These methods are believed to function according to the principles described in WO 92/20703 (herein incorporated by reference) by replacing the compounds used in the prior art with the compounds described herein above. It is especially preferred to use a nucleic acid mimic which is labeled with a reporter group either at one of the termini of the nucleic acid mimic or at any position of the backbone or the base moieties. A reporter group according is a group that can be detected, for example a fluorescent group like fluorescein, or one which can be detected by a further compound which is bound in a subsequent step to the reporter group. For example, if the sterically bulky substituent is a biotin group or a group containing a biotin group, the nucleic acid mimic, and thereby the nucleic acid can be determined by adding detectable streptavidin to the hybrid. It is preferred to remove any excess biotin-labeled nucleic acid mimic from the mixture prior to this incubation. The reporter group is then detected by means which are known to the art-skilled.

The present invention is suitable for detection of expression of a disease-causing protein in a cell or tissue sample from patients who have a disease state. A number of assays may be formulated for the inhibition of protein expression employing the present invention, which assays will commonly comprise contacting a cell or tissue sample with a nucleic acid mimic of the invention under conditions selected to permit detection, and usually quantitation, of such inhibition. As described below, fluorescein-labeled nucleic acid mimics are prepared and contacted with a cell or tissue sample suspected of expression of a disease-causing protein. The sample is then washed to remove unbound nucleic acid mimic. Fluorescence remaining in the sample, detected and quantitated by fluorimetry, indicates bound nucleic acid mimic (which in turn indicates the presence of nucleic acid encoding the disease-causing protein).

The compounds of the present invention may be useful in binding to target molecules. Target molecules of the present invention can include any of a variety of biologically significant molecules. Such target molecules may be nucleic acid strands such as significant regions of DNA or RNA which encode proteins that may be responsible for causing and/or maintaining a disease state in mammals. Such other target molecules may be transcription factors. Target molecules can be carbohydrates, glycoproteins or other proteins. In some preferred embodiments, the target molecule can be a protein such as an immunoglobulin, receptor, receptor binding ligand, antigen or enzyme, and more specifically can be a phospholipase, tumor necrosis factor, endotoxin, interleukin, plasminogen activator, protein kinase, cell adhesion molecule, lipoxygenase, hydrolase or transacylase. In other embodiments of the invention, the target molecule may be an important region of the human immunodeficiency virus, Can-

*dida,* herpes viruses, papillomaviruses, cytomegalovirus, rhinoviruses, hepatitis viruses or influenza viruses. In yet other embodiments of the invention, the target molecule may be a region of an oncogene.

The following examples further illustrate the invention and are not intended to limit the same.

EXAMPLES

Example 1

A. Exemplary General Syntheses

Phosphoramidates were purchased from Cruachem (UK) and the DNA oligomers were assembled on a MilliGen/Biosearch 8700 DNA synthesizer. The A, C, G and T PNA monomers were purchased from Biosearch (USA). N'-Boc-aminoethyl glycine was purchased from Biosearch (USA). All PNA oligomers were synthesized on a custom-made PNA synthesizer (Biosearch, USA) by a modified Merrifield method (Christensen, L., Fitzpatrick, R., Gildea, B., Warren, B. and Coull, J. (1994), Innovations and Perspectives in Solid Phase Synthesis, R. Epton, Ed., SPCC (UK) Ltd., Oxford, England; Christensen et al., (1995), J. Pep. Sci., 3, 175) and purified by reverse phase-HPLC. The PNA oligomers were characterized by FAB$^+$MS.

B. $T_m$ Measurements

Absorbance versus temperature was measured at 260 nm using a Guilford Response spectrophotometer. Heating rate was 0.5° C./min from 5-90° C. PNA oligomers were hybridized with complementary DNA sequences in a medium salt buffer containing 100 mM NaCl, 10 mM sodium phosphate and 0.1 mM EDTA, pH was adjusted to 5, 7 or 9, as desired. The samples were heated to 90° C. for 5 min, slowly cooled to 20° and left at 4° C. for 30 min prior to $T_m$ measurements.

C. Synthesis of Modified Cytosine Monomer (i) Benzoyl cytosin-1-ylacetate (1)

Reference is made to FIG. 1 where to cytosine (20 g, 0.18 mmol) in 400 mL DMF was added 7.2 g (0.18 mmol) of NaH (disp. in oil 60%). The mixture was heated to 50° C. and stirred for 2 h under nitrogen. After cooling to room temperature, 29 mL (1.1 eq.) of benzyl bromoacetate was added over 2 h. After stirring overnight, the dark suspension was filtered and the filtrate washed with cold DMF and 0.2 M sodium bicarbonate. The product (1) was crystallized from ethanol. Yield: 37 g (79%). $^1$H NMR (d$_6$-DMSO): δ 4.56 (s, 2 CH$_2$O), 5.24 (s, 2 H, CH$_2$CO), 5.77 (d, 1 H, H$_5$), 7.20 (dd, 2 H, NH$_2$), 7.45 (m, 5 H, aromatic), 7.65 (d, 1 H, H$_6$). MS (FAB) m/z 260 (M+H)$^+$ (calcd 260).

(ii) (N$^4$-(Benzoyl)cytosin-1 yl)acetic Acid (2)

To a solution of (1) (10 g, 38 mmol) in 10 mL pyridine was added 6.6 g (47 mmol) of benzoyl chloride and stirred overnight at room temperature. The solution was evaporated under reduced pressure. The residue was dissolved in 1 M KOH and stirred for 3 h after which the Ph was adjusted to 2 with conc. HCl. The target compound (2) precipitated out. Yield: 9.3 g (90%). $^1$H NMR (d$_6$-DMSO): δ 4.59 (s, 2 H, CH$_2$O), 7.31 (d, 1 H, H$_5$), 7.5-8.2 (7 H, aromatic, NH, H$_6$). MS (FAB) m/z 273 (M+H)$^+$ (calcd 273).

(iii) N-((N$^4$-(Benzoyl)cytosin-1-yl)acetyl)-N-(2-Boc-aminoethyl)glycine (3)

4.8 g (22 mmol) of Methyl N-(2-Boc-aminoethyl)glycinate (2), 2.4 g (14.7 mmol) of benzyloxycarbonyl chloride, 2.9 g (14.9 mmol) of DCC and 2.4 g (14.7 mmol) of DhBtOH was dissolved in 50 mL of DMF and stirred for 4 h at room temperature. Dichloromethane (100 mL) was added and the mixture extracted with 3×0.2 M sodium bicarbonate, 2×1 M sodium hydrogen sulfate and brine. The organic phase was dried with magnesium sulfate and evaporated to dryness under reduced pressure. The residue was dissolved in 2 M KOH and stirred for 1 h after which the pH was adjusted to 2 with 1 M HCl, whereby the target compound precipitated. The product (3) was crystallized from methanol:ethyl acetate: hexane (1:2:2). Yield: 4.2 g (60%). $^1$H NMR (d$_6$-DMSO): δ 1.45 and 1.47 (d, 9 H, Boc), 3.28-3.53 (m, 4 H, CH$_2$), 4.08 and 4.31 (s, 2 H, CH$_2$CO), 4.75 and 4.95 (s, 2 H, CH$_2$CO), 6.83 and 7.03 (m, 1 H, BocN$\underline{H}$), 7.38 (m, 1 H, H$_5$), 7.57-8.10 (m, 6 H, aromatic and H$_6$). MS (FAB) m/z 474 (M+H)$^+$ (calcd 474).

Example 2

Triplex Inhibition

The effect of the benzoylated cytosine (C$^{Bz}$) residue on the hybridization properties of a homopyrimidine peptide nucleic acid was studied. PNA1, H-TTTTCCTCTC-LysNH$_2$, (SEQ ID NO:3) was synthesized containing either C$^{Bz}$ in position 6 (PNA2), or two C$^{Bz}$ residues in positions 6 and 8 (PNA3) or in positions 5 and 6 (PNA4). These PNAs were hybridized to a complementary oligonucleotide in the parallel (ODN1) or the antiparallel (ODN2) configuration and the thermal stability ($T_m$) of the resulting complexes was determined at pH 5-9. The results are set forth in Table 1. Absorbance versus temperature curves were measured at 260 nm in 100 mM NaCl, 10 mM sodium phosphate and 0.1 mM EDTA. Heating rate: 0.5°/minute at 5-90° C. The $T_m$s in parentheses were obtained by cooling from 90° to 10° C. while measuring the absorbance at 260 nm.

TABLE 1

Melting temperatures $T_m$ (° C.) for binding of PNA to single stranded homopurine DNA oligomer.

|      | ODN1        | ODN2        | pH |
|------|-------------|-------------|----|
|      | PNA3        | 58.5 (31.0) | 5  |
|      |             | 26.0        |    |
|      |             | 40.5        | 7  |
|      |             | 33.5        | 9  |
| PNA2 | 56.0 (38.0) | 54.0 (42.5) | 5  |
|      | 27.0 (20.0) | 32.0 (29.0) | 7  |
|      | —           | 31.0 (29.0) | 9  |
| PNA3 | 28.0        | 33.0        | 7  |
| PNA4 | 26.0        | 32.5        | 7  |

Oligodeoxynucleotides:
ODN1=5'-AAAAGGAGAG-3' SEQ ID NO:1
ODN2=5'-GAGAGGAAAA-3' SEQ ID NO:2

Nucleic acid mimics:
PNA1=H-TTTTCCTCTC-LysNH$_2$ SEQ ID NO:3
PNA2=H-TTTTCC$^{Bz}$TCTC-LysNH$_2$ SEQ ID NO:4, where C$^{Bz}$ is N
PNA3=H-TTTTCC$^{Bz}$TC$^{Bz}$TC-LysNH$_2$ SEQ ID NO:5, where C$^{Bz}$ is N
PNA4=H-TTTTC$^{Bz}$C$^{Bz}$TCTC-LysNH$_2$ SEQ ID NO:6, where C$^{Bz}$ is N Unmodified PNA1 exhibited expected behaviour. First, pronounced pH dependence was observed which is compatible with PNA$_2$-DNA triplex formation requiring cytosine protonation. Second, the parallel complex showed highest stability at pH 5 and 7, but not at pH 9. These results suggest that triplexes are the most stable complexes at pH 5 and 7, while the (antiparallel) duplex is more stable at pH 9. Triplex formation at pH 7 is also consistent with pronounced hysteresis (≈27° C.) observed at this pH.

PNA2, containing one $C^{Bz}$ residue, apparently also formed a triplex at pH 5 as judged by the hysteresis, but the $T_m$ was lower (≈30° C.) than that of the PNA1 complex. Thus, the benzoyl groups do indeed appear to interfere with efficient triplex formation. This effect is especially pronounced at pH 7. Only slight hysteresis is observed and notably the antiparallel complex shows higher stability which does not decrease at more alkaline conditions (pH 9). These results strongly argue in favour of the duplex being the most stable complex at pH 7 with this PNA.

The complexes with PNA1 and PNA2 showed equal thermal stability at pH 9, i. e. for the duplex, thus indicating that the $C^{Bz}$ residue does not interfere with Watson-Crick base pairing in the PNA-DNA duplex. This conclusion was supported by experiments with a $C^{Bz}$ containing mixed purine/pyrimidine sequence using the PNA oligomers H-AGT CAC CTA C-LysNH$_2$ (PNA5) SEQ ID NO:9 and H-AGT CA $C^{Bz}$ CTA C-LysNH$_2$ (PNA6) SEQ ID NO:10, and is set forth in Table 2. Absorbance versus temperature curves were measured at 260 nm in 100 mM NaCl, 10 mM sodium phosphate and 0.1 mM EDTA, at pH 7. Heating rate: 0.5%/min at 5-90° C. The $T_m$s in parentheses were obtained by cooling from 90 to 10° C. while measuring the absorbance at 260 nm. The hysteresis of the system is the difference between the $T_m$ (10-90°) and $T_m$ (90-10°).

TABLE 2

Melting temperatures $T_m$ (° C.) for binding of PNA in duplex mode to single-stranded DNA oligomer.

|  | PNA5 | PNA6 |
|---|---|---|
| ODN3 | 49 (48) | 50 |
| ODN4 | 33 (31) | 34 |

Oligodeoxynucleotides:
ODN3=5'-GTAGGTCACT-3' SEQ ID NO:7
ODN4=5'-GTAGATCACT-3' SEQ ID NO:8

Figure 2:
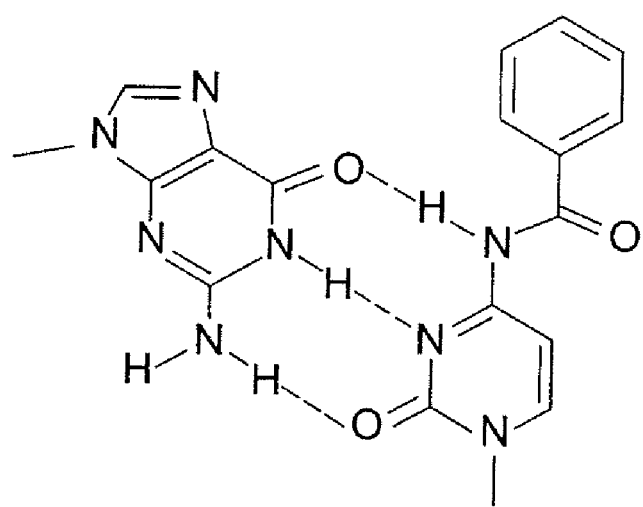
FIG. 2 is a schematic illustrating the Watson-Crick base pairing between $N^4$ substituted cytosine of a PNA and guanosine of a DNA.

Nucleic acid mimics:
PNA5=H-AGTCACCTAC-LysNH$_2$ SEQ ID NO:9
PNA6=H-AGTCAC$^{Bz}$CTAC-LysNH$_2$ SEQ ID NO:10, where $C^{Bz}$ is N Both of these oligomers form highly stable duplexes with their antiparallel oligonucleotide target. The stoichiometry of these complexes was determined by Job-plots as 1:1 complexes in both cases. The insignificant difference in $T_m$s of the complexes between PNA5 and PNA6 with ODN3 falls within experimental error and can be interpreted as evidence of the structure shown in FIG. 2, by which the benzoyl group is positioned in the major groove not interfering with the Watson-Crick base pairing. This is also in full agreement with the (G→A) mismatch positioned opposite the cytosine in the DNA strand, giving rise to a drop in $T_m$ of 15-16° for both PNA5 and PNA6. An important feature distinguishing duplexes from triplexes under the experimental conditions is the very small hysteresis (less than 2°) obtained with duplexes when going from high to low temperature, whereas PNA: DNA triplexes showed pronounced hysteresis typically in the range of 20-30° (Table 2). This is also evident for the complexes between PNA6 and ODN3 or ODN4 in which a hysteresis of 1-2° C. was observed. The small hysteresis obtained with PNA6 also indicated that the benzoyl group does not interfere significantly with the binding kinetics.

Example 3

Coupling of Nucleic Acid Mimic to Fluorescein

A nucleic acid mimic having a free amine moiety is dissolved in THF:H$_2$O to provide a solution that is 0.1 M of nucleic acid mimic. To the nucleic acid mimic solution is added fluorescein isothiocyanate, providing a solution that is 0.1-1.0 M in fluorescein isothiocyanate. The resultant reaction mixture is stirred for 0.1-2 hours and concentrated under reduced pressure. The residue is purified by preparative HPLC.

Example 4

Detection of Mutant β-amyloid Precursor Protein Gene Expression (βAPP)

Point mutations in the gene, encoding β-amyloid have been implicated in familial Alzheimer's disease (FAD). Nucleic acid mimics are labeled with fluorescein or other fluorescent tags, as illustrated in Example 3 above. The fluorescently-labeled nucleic acid mimics are contacted with a cell or tissue sample suspected of abnormal βAPP expression under conditions suitable for specific hybridization of the nucleic acid mimic to the nucleic acid encoding abnormal βAPP. The sample is then washed to remove unbound nucleic acid mimics. Label remaining in the sample indicates bound nucleic acid and is quantitated using a fluorimeter, fluorescence microscope or other routine means.

A first sample of cells or tissues suspected of expressing a point mutation in the βAPP gene is incubated with a fluorescein-labeled nucleic acid mimic which is targeted to the mutant codon 717, codon 670 or codon 671 of the βAPP mRNA. A second identical sample of cells or tissues is incubated with a second labeled nucleic acid mimic which is targeted to the same region of normal βAPP mRNA under conditions in which specific hybridization can occur. The sample is then washed to remove unbound nucleic acid mimic. Label remaining in the sample indicates bound nucleic acid and is quantitated using a fluorimeter or other routine means. The presence of mutant βAPP is indicated if the first sample retains labeled nucleic acid mimic and the second sample does not retain labeled nucleic acid mimic.

Example 5

Detection of Mutant H-ras Gene Expression

Point mutations in the H-ras gene have been implicated in numerous aberrations of the ras pathway. Nucleic acid mimics are labeled with fluorescein or other fluorescent tags as illustrated in Example 3 above. Labeled nucleic acid mimics are contacted with cell or tissue samples suspected of abnormal ras expression under conditions in which specific hybridization can occur. The sample is then washed to remove unbound labeled nucleic acid mimic. Label remaining in the sample indicates bound nucleic acid (i.e. that which encodes for mutant ras) and is quantitated using a fluorimeter, fluorescence microscope or other routine means.

A first cell or tissue sample suspected of expressing a point mutation in the H-ras gene is incubated, under conditions suitable for specific hybridization, with a fluorescein-labeled nucleic acid mimic which is targeted to codon 12, codon 13 or codon 61 of mutant H-ras mRNA. A second identical sample of cells or tissues is incubated, under conditions suitable for specific hybridization, with a second fluorescently-labeled nucleic acid mimic which is targeted to the same region of normal H-ras mRNA. The samples are then washed to remove unbound labeled nucleic acid mimics. Label remaining in the sample indicates bound nucleic acid and is quantitated using a fluorimeter or other routine means. The presence of mutant H-ras is indicated if the first sample exhibits fluorescence but the second sample does not.

Example 6

Inhibition of Gene Expression by Nucleic Acid Mimics

A preferred assay to test the ability of nucleic acid mimics to inhibit expression of the E2 mRNA of papillomavirus is based on the well-documented transactivation properties of E2. Spalholtz et al., J. Virol., 61, 2128 (1987). A reporter plasmid (E2RE1CAT) is constructed to contain the E2 responsive element, which functions as an E2-dependent enhancer. E2RE1CAT also contains the SV40 early promoter, an early polyadenylation signal and the chloramphenicol acetyl transferase (CAT) gene. Within the context of this plasmid, CAT expression is dependent upon expression of E2. The dependence of CAT expression upon the presence of E2 is tested by transfection of this plasmid into C127 cells transformed by BPV-1, uninfected C127 cells and C127 cells cotransfected with E2RE1CAT and an E2 expression vector.

A. Inhibition of BPV-1 E2 expression: BPV-1 transformed C127 cells are plated in 12-well plates. Twenty four hours prior to transfection with E2RE1CAT, cells are pretreated by the addition of complementary nucleic acid mimic to the growth medium at a final concentrations of 5, 15 and 30 mM. The next day, cells are transfected with 10 µg of E2RE1CAT by calcium phosphate precipitation. E2RE1CAT (10 µg) and carrier DNA (PUC 19, 10 µg) are mixed with 62 µL of 2 M $CaCl_2$ in a final volume of 250 µL of $H_2O$, followed by the addition of 250 µL of 2×HBSP (1.5 mM $Na_2PO_4$, 10 mM KCl, 280 mM NaCl, 12 mM glucose and 50 mM HEPES, pH 7.0) and incubated at room temperature for 30 minutes. This solution (100 µL) is added to each test well and allowed to incubate for 4 hours at 37° C. After incubation, the cells are glycerol shocked for 1 minute at room temperature with 15% glycerol in 0.75 mM $Na_2PO_4$, 5 mM KCl, 140 mM NaCl, 6 mM glucose and 25 mM HEPES, pH 7.0. After shocking, the cells are washed 2× with serum-free DMEM and refed with DMEM containing 10% fetal bovine serum and nucleic acid mimic at the original concentration. Forth eight hours after transfection, the cells are harvested and assayed for CAT activity.

For determination of CAT activity, cells are washed 2× with phosphate-buffered saline and collected by scraping. Cells are suspended in 100 µL of 250 mM Tris-HCl, pH 8.0, and disrupted by freeze-thawing three times. This cell extract (25 µL) is used for each assay.

For each assay, the following are mixed together in a 1.5 mL Eppendorf tube and incubated at 37° C. for one hour: 25 µL of cell extract, 5 µL of 4 mM acetyl coenzyme A, 18 µL of $H_2O$ and 1 µL of $^{14}C$-chloramphenicol, 40-60 mCi/mM. After incubation, chloramphenicol (acetylated and non-acetylated forms) is extracted with ethyl acetate and evaporated to dryness. Samples are resuspended in 25 µL of ethyl acetate, spotted onto a tlc plate and chromatographed in chloroform:methanol (19:1). The chromatographs are analyzed by autoradiography. Spots corresponding to acetylated and non-acetylated $^{14}C$-chloramphenicol are excised from the tlc plate and counted by liquid scintillation for quantitation of CAT activity. Nucleic acid mimics that depress CAT activity in a dose-dependent manner are considered to have a positive effect.

Inhibition of HPV E2 expression: The assay for inhibition of human papillomavirus (HPV) E2 by nucleic acid mimics is essentially the same as that for BPV-1 E2. For HPV assays, appropriate HPVs are cotransfected into either CV-1 or A431 cells with PSV2NEO using the calcium phosphate method described above. Cells which take up DNA are selected for culturing in media containing the antibiotic G418. G418-resistant cells are then analyzed for HPV DNA and RNA. Cells expressing E2 are used as target cells for complementary studies. For each nucleic acid mimic, cells are pretreated as above, transfected with E2RE1CAT and analyzed for CAT activity as described above. Nucleic acid mimics are considered to have a positive effect if they can depress CAT activity in a dose-dependent manner.

---

What is claimed is:

1. A nucleic acid mimic in admixture with at least one target molecule selected from the group consisting of nucleic acids, transcription factors, carbohydrates and proteins, said mimic having formula (I):

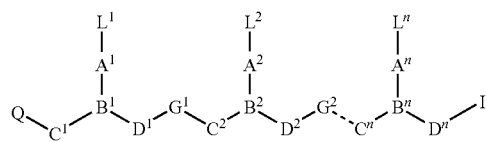

(I)

wherein:
n is at least 2,
each of $L^1$-$L^n$ is independently selected from the group consisting of hydrogen, hydroxy, $(C_1$-$C_4)$alkanoyl, naturally occurring nucleobases, non-naturally occurring nucleobases, aromatic moieties, DNA intercalators, nucleobase-binding groups, heterocyclic moieties, and reporter ligands, at least one of $L^1$-$L^n$ being said base substituted with at least one sterically bulky substituent;
each of $C^1$-$C^n$ is $(CR^6R^7)_y$, where $R^6$ is hydrogen and $R^7$ is selected from the group consisting of the side chains of naturally occurring alpha amino acids, or $R^6$ and $R^7$ are independently selected from the group consisting of hydrogen, $(C_2$-$C_6)$alkyl, aryl, aralkyl, heteroaryl, hydroxy, $(C_1$-$C_6)$alkoxy, $(C_1$-$C_6)$alkylthio, $NR^3R^4$ and $SR^5$, where $R^3$ and $R^4$ independently are hydrogen, a conjugate, $(C_1$-$C_4)$alkyl, hydroxy- or alkoxy- or alkylthio-substituted $(C_1$-$C_4)$alkyl, hydroxy, alkoxy, alkylthio or amino; and $R^5$ is hydrogen, $(C_1$-$C_6)$alkyl, hydroxy-, alkoxy-, or alkylthio-substituted $(C_1$-$C_6)$ alkyl, or $R^6$ and $R^7$ taken together complete an alicyclic or heterocyclic system;
each of $D^1$-$D^n$ is $(CR^6R^7)_z$ where $R^6$ and $R^7$ are as defined above;
each of y and z is zero or an integer from 1 to 10, the sum y+z being greater than 2 but not more than 10;
each of $G^1$-$G^{n-1}$ is —$NR^3$CO—, —$NR^3$CS—, —$NR^3$SO— or —$NR^3$SO$_2$—, in either orientation, where $R^3$ is as defined above;
each pair of $A^1$-$A^n$ and $B^1$-$B^n$ are selected such that:
 (a) A is a group of formula (IIc) and B is N or $R^3N^+$; or
 (b) A is a group of formula (IId) and B is CH;

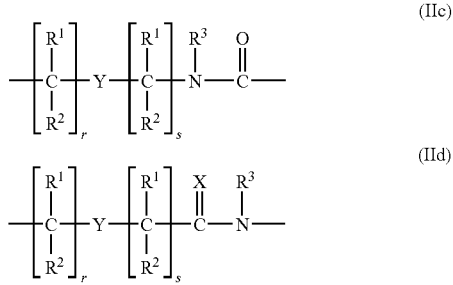

where:
X is O, S, Se, $NR^3$, $CH_2$ or $C(CH_3)_2$;
Y is a single bond, O, S or $NR^4$;
each of p and q is zero or an integer from 1 to 5.

2. The nucleic acid mimic according to claim 1 wherein said target molecule is a nucleic acid.

3. The nucleic acid mimic according to claim 1 wherein said sterically bulky substituent has 3 or more non-hydrogen atoms and is —R', —OR', —SR', —N(R')$_2$, —C(R')$_3$, —C(=X)(R'), —C(=X)(—Y—R') or S(=O)$_{1\text{-}2}$(—Y—R') wherein:
X is O, S or NH;
Y is O, S or NH; and
R' is H, $C_1$-$C_{50}$-alkyl, $C_2$-$C_{50}$-alkenyl, $C_2$-$C_{50}$-alkynyl, $C_7$-$C_{50}$-alkyl-aryl, $C_6$-$C_{50}$-aryl, $C_{10}$-$C_{50}$-naphthyl, $C_{12}$-$C_{50}$-biphenyl, $C_7$-$C_{50}$-aryl-alkyl, pyridyl, imidazolyl, pyrimidinyl, pyridazinyl, quinolyl, acridinyl, pyrrolyl, furanyl, thienyl, isoxazolyl, oxazolyl, thiazolyl and biotinyl, wherein R' can be substituted one or more times by —NO, —NO$_2$, —SO$_3$, —CN, —OH, —NH$_2$, —SH, —PO$_3^{2-}$, —COOH, —F, —Cl, —Br and —I.

4. The nucleic acid mimic according to claim 1 wherein said base is a naturally or non-naturally occurring pyrimidine base.

5. The nucleic acid mimic according to claim 4 wherein said sterically bulky substituent is bound to C-6, C-5 or N-4 of said naturally occurring pyrimidine base.

6. The nucleic acid mimic according to claim 5 wherein said sterically bulky substituent is bound to N-4 of said naturally occurring pyrimidine base.

7. The nucleic acid mimic according to claim 6 wherein said naturally occurring pyrimidine base is cytosine.

8. The nucleic acid mimic according to claim 6 wherein said sterically bulky substituent is (C=O)—R" wherein R" is $C_1$-$C_{20}$-alkyl or $C_6$-$C_{18}$-aryl.

9. The nucleic acid mimic according to claim 8 wherein said sterically bulky substituent is (C=O)—$C_6H_5$.

10. The nucleic acid mimic according to claim 1 having formula (IIIa):

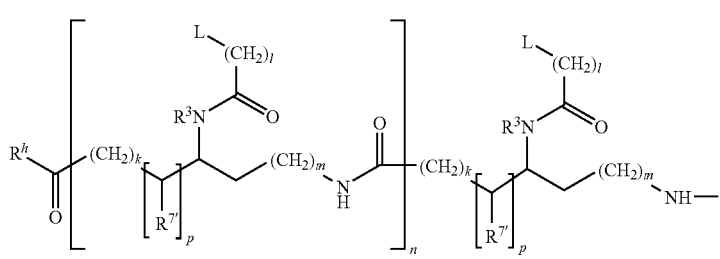

(IIIa)

wherein:
each L is independently selected from the group consisting of hydrogen, phenyl, heterocyclic base moieties, including those substituted with a sterically bulky group or groups, naturally occurring nucleobases, and non-naturally occurring nucleobases, at least one L being said base substituted with at least one sterically bulky substituent;

$R^3$ and $R^4$ independently are hydrogen, a conjugate, $(C_1\text{-}C_4)$alkyl, hydroxy- or alkoxy- or alkylthio-substituted $(C_1\text{-}C_4)$alkyl, hydroxy, alkoxy, alkylthio or amino;

each $R^{7'}$ is independently selected from the group consisting of hydrogen and the side chains of naturally occurring alpha amino acids;

n is an integer from 1 to 60;

each of k, l, and m is independently zero or an integer from 1 to 5;

p is zero or 1;

$R^h$ is OH, $NH_2$ or —$NHLysNH_2$; and $R^i$ is H or $COCH_3$.

11. The nucleic acid mimic according to claim 1 having formula (IIIb):

ing those substituted with a sterically bulky group or groups, naturally occurring nucleobases, and non-naturally occurring nucleobases, at least one L being said base substituted with at least one sterically bulky substituent;

$R^3$ and $R^4$ independently are hydrogen, a conjugate, $(C_1\text{-}C_4)$alkyl, hydroxy- or alkoxy- or alkylthio-substituted $(C_1\text{-}C_4)$alkyl, hydroxy, alkoxy, alkylthio or amino;

each $R^{7'}$ is independently selected from the group consisting of hydrogen and the side chains of naturally occurring alpha amino acids;

n is an integer from 1 to 60;

each of k, l, and m is independently zero or an integer from 1 to 5;

p is zero or 1;

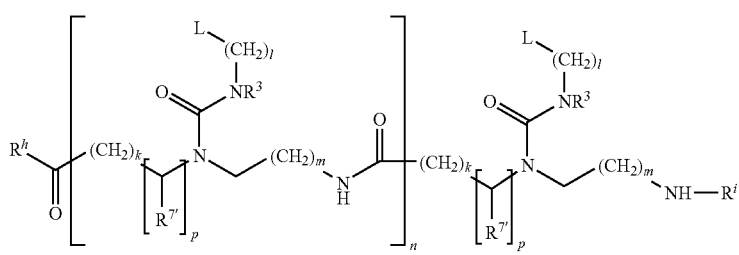

(IIIb)

wherein:
each L is independently selected from the group consisting of hydrogen, phenyl, heterocyclic base moieties, including $R^h$ is OH, $NH_2$ or —$NHLysNH_2$; and $R^i$ is H or $COCH_3$.

* * * * *